United States Patent
Harats et al.

(10) Patent No.: US 7,279,459 B2
(45) Date of Patent: *Oct. 9, 2007

(54) METHODS EMPLOYING AND COMPOSITIONS CONTAINING PLAQUE ASSOCIATED MOLECULES FOR PREVENTION AND TREATMENT OF ATHEROSCLEROSIS

(75) Inventors: Dror Harats, Ramat Gan (IL); Jacob George, Petah Tikva (IL)

(73) Assignee: Vascular Biogenics Ltd., Or Yehuda (IL)

( * ) Notice: Subject to any disclaimer, the term of this patent is extended or adjusted under 35 U.S.C. 154(b) by 312 days.

This patent is subject to a terminal disclaimer.

(21) Appl. No.: 10/451,370

(22) PCT Filed: Jan. 3, 2002

(86) PCT No.: PCT/IL02/00005

§ 371 (c)(1),
(2), (4) Date: Jul. 2, 2003

(87) PCT Pub. No.: WO02/053092

PCT Pub. Date: Jul. 11, 2002

(65) Prior Publication Data

US 2004/0047870 A1    Mar. 11, 2004

Related U.S. Application Data

(60) Provisional application No. 60/259,512, filed on Jan. 4, 2001.

(51) Int. Cl.
*A61K 38/17* (2006.01)
(52) U.S. Cl. ........................................ 514/12
(58) Field of Classification Search ............... 435/6
See application file for complete search history.

(56) References Cited

U.S. PATENT DOCUMENTS

| | | | |
|---|---|---|---|
| 4,874,769 A | 10/1989 | Youssefyeh et al. | |
| 4,874,795 A | 10/1989 | Yesair | |
| 5,348,945 A | 9/1994 | Berberian et al. | |
| 5,409,710 A | 4/1995 | Leonard | |
| 6,225,070 B1 | 5/2001 | Witztum et al. | |
| 6,497,880 B1 * | 12/2002 | Wisniewski | 424/190.1 |
| 6,541,011 B2 | 4/2003 | Punnonen et al. | |

| | | |
|---|---|---|
| 2003/0114367 A1 | 6/2003 | Schoenfeld et al. |
| 2005/0148499 A1 | 7/2005 | Harats et al. |
| 2005/0197283 A1 | 9/2005 | Harats et al. |

FOREIGN PATENT DOCUMENTS

| | | |
|---|---|---|
| WO | WO 98/16248 | 4/1998 |
| WO | WO 00/20019 | 4/2000 |
| WO | WO 01/68119 | 9/2001 |
| WO | WO 01/68124 | 9/2001 |

OTHER PUBLICATIONS

Lindquinst et al., Ann. Rev. Biochem, 1986, vol. 55, pp. 1151-1191.*
Schlesinger, et al., J. Cell Biol., 1986, vol. 103, pp. 321-325.*
Palinski et al., Proc. Natl. Acad. Sci., 1995, vol. 92, pp. 821-825.*
Ameli et al., Arteriosclerosis, Thrombosis, and Vascular Biology, 1996, vol. 16, pp. 1074-1079.*
Kobayashi et al., Journal of Lipid Research, 2001, vol. 42, pp. 697-709.*
Xu et al., Arteriosclerosis and Thrombosis, 1992, vol. 12, pp. 789-799.*
Xiao et al., Clincial Immunology and Immunopathology, 1997, vol. 85, pp. 119-128.*
George et al. "Hyperimmunization of Apo-E-Deficient Mice With Homologous Malondialdehyde Low-Density Lipoprotein Suppresses Early Atherogenesis", Atherosclerosis, 138: 147-152, 1998.
Bonnin et al. "Mucosol Modulation of Immune Responses to Heat Shock Proteins in Autoimmune Arthritis", Biotherapy, 10(3); 213-221, 1998. Abstract.
George et al. "Induction of Early Atherosclerosis in LDL-Receptor Deficient Mice Immunized With β2-Glycoprotein I", Circulation, 98: 1108-1115, 1998.
George et al. "Altherosclerosis-Related Markers in Systematic Lupus Erythematosus Patients: The Role of Humoral Immunity in Enhanced Atherogenesis", Lupus, 8: 220-226, 1999.
Hansson et al. "Autoimmunity In Atherosclerosis", Atherosclerosis, 134 (1-2): 289, 1997. Abstract. & 11th International Symposium on Atherosclerosis, p. 289, 1997.
Sima et al. "Modified Lipoproteins Generate Autoantibodies and Accumulate in the Arterial Lesions of Athero-Diabetic Patients and Hamsters", Atherosclerosis, 134 (1-2): 227, 1997. Abstract. & 11th International Symposium on Atherosclerosis, p. 227, 1997. Abstract.
Resch et al. "Competition-Studies With Antioxidized LDL Autoantibodies", Atheresclerosis, 132 (1-2): 227, 1997. Abstract.

(Continued)

*Primary Examiner*—Robert A Wax

(57) ABSTRACT

Methods and compositions employing plaque associated molecules effective in inducing mucosal tolerance and inhibiting inflammatory processes contributing to atheromatous vascular disease and sequalae are provided.

8 Claims, 2 Drawing Sheets

OTHER PUBLICATIONS

McKown et al. "Lack of Efficacy of Oral Bovine Type II Collagen Added to Existing Therapy in Rheumatoid Arthritis", Journal of Arthritis & Rheumatism, 42(6): 1204-1208, 1999.

Spack et al. "Antigen-Specific Therapies for the Treatment of Multiple Sclerosis: A Clinical Trial Update", Expert Opinion on Investigational Drugs, 6(11): 1715-1727, 1997.

Lymaye et al. "Evaluation of Antibodies to β2-Glycoprotein 1 in the Causation of Coronary Atherosclerosis as Part of the Antiphospholipid Syndrome", AU/NZ Journal of Medicine, 29: 789-793, 1999.

Blanas et al. "Induction Autoimmune Diabetes by Oral Administration of Autoantigen" Science, 274(5293): 1707. Abstract.

Pech et al. "LDL Modifiées et Athérosclérose. Nature des Modifications. Propriétés Physicochimiques et Biologiques". Ann. Biol. Clin., 50: 213-227, 1992.

Hoff et al. "Structure of Cholesterol-Containing Particles Accumulating in Atherosclerotic Lesions and Mechanisms of Their Derivation", Current Opinion in Lipidologya, 6: 317-325, 1995.

Shen et al. "From Interaction of Lipidic Vehicles With Intestinal Epithelial Cell Membranes to the Formation and Secretion of Chylomicrons", Advanced Drug Delivery Reviews, 50: S103-S125, 2001.

Maurer et al. "Developments in Liposomal Drug Delivery Systems", Expert Opinion Biol. Ther., 1(6): 1-24, 2001.

Emeson et al. "Accelerated Atherosclerosis in Hyperlipidemic C57BL/6 Mice Treated With Cyclosporin A", American Journal of Pathology, 142(6): 1006-, 1993.

Meir et al. "Inflammation in Atherosclerosis—Causal or Casual ? The Need for Randomized Trials of Anti-Inflammatory Agents", Department of Medicine B, Hadassah University Hospital.

Williams "Rodent Models of Arthritis: Relevance for Human Disease", Clin. Exp. Immunol., 114: 330-332, 1998.

Fujinami et al. "Myelin Basic Protein Serum Factor—An Endogenous Neuroantigen Influencing Development of Experimental Allergic Ecephalomyelitis Allergic Encephalomyelitis in Lewis Rats", Journal Exp. Med. , 148: 1716-1721, 1978.

Ogra et al. "Vaccination Strategies for Mucosol Immune Responses", Clinical Microbiology Review, p. 430-445, 2001.

Lehner et al. "The Effect of Route of Immunzation on Mucosol Immunity and Protection", The Journal of Infectious Diseases, 179(Suppl 3):S489-S492, 1999.

Chen "Recent Advances in Mucosol Vaccine Development", Journal of Controlled Release, 67: 117-128, 2000.

Freigang et al. "Immunization of LDL Receptor-Deficient Mice With Homologous Malondialdehyde-Modified and Native LDL Reduces Progression of Atherosclerosis by Mechanisms Other Than Induction of High Titers of Antibodies to Oxidative Neopitopes", Arterioscler. Thromb. Vasc. Biol., 18: 1972-1982, 1998.

Zhou et al. "LDL Immunization Induces T-Cell-Dependent Antibody Formation and Protection Against Atherosclerosis", Arteriscler. Thromb. Vasc. Biol., 21: 108-114, 2001.

Mol et al. "The Role of Modification of Lipoproteins and of the Immune System in Early Atherogenesis", Netherland Journal of Medicine, 43(1-2): 83-90, 1993.

Resch et al. "Competition-Studies With Antioxidized LDL Autoantibodies", 11th International Symposium on Atherosclerosis, Paris, 3.P.138, p. 227, 1997. Abstract.

Shen et al. "A Delayed Transient Elevation of Protein Kinase C Activity Is Associated With Oxidized Liporotein(a)-Induced Production of Plasminogen Activator Inhibitor-1 in Vascular Endothelial Cells", 11th International Symposium on Atherosclerosis, Paris, 3.P.137, p. 227, 1997, Abstract.

Tertov et al. "Atherogenicity of Low Density Lipoprotein Does Not Correlate With The Degree of Its Oxidation", 11th International Symposium on Atherosclerosis, Paris, 3.P.139, p. 227, 1997. Abstract.

Matsuura et al "Are Oxidized LDL/β2-Glycoprotein I Complexes Pathogenic Antigens in Autoimmune-Mediated Atherosclerosis?", Clinical Development Immunology, 11(2): 103-11, 2004. Abstract.

Cockerill et al. "Detection and Characterization of B Cell Epitopes on β2-Glycoprotein I", Clinical Immunology, 112(2): 129-135, 2004. Abstract.

George et al. "Adoptive Transfer of β2-Glycoprotein I-Reactive Lymphocytes Enhances Early Atherosclerosis in LDL Receptor-Deficient Mice", Circulation, 102: 1822-1827, 2000.

George et al. "Suppression of Early Atherosclerosis in LDL-Receptor Deficient Mice by Oral Tolerance With β2-Glycoprotein I", Cardiovascular Research, 62: 603-609, 2004.

Vaarala et al. "Antibodies to Prothrombin Imply A Risk of Myocardial Infarction in Middle-Aged Men", Thrombosis and Haemostasis, 75(3): 456-459, 1996.

George et al. "The Prediction of Coronary Atheresclerosis Employing Artifical Neural Networks", Clinical Cardiology, 23: 453-456, 2000.

Sherer et al. "Coronary Artery Disease But Not Coronary Calcification Is Associated With Elevated Levels of Cardiolipin, β2-Glycoprotein-I, and Oxidized LDL Antibodies", Cardiology, 95: 20-24, 2001.

Sherer et al. "Autoantibodies to Cardiolipin and β-2-Glycoprotein-I in Coronary Artery Disease Patients With and Without Hypertension", Cardiology, 97: 2-5, 2002.

Kroeger et al. "Autoantibodies and Peripheral Arterila Occlusive Disease", Herz, 29(1): 26-31, 2004. Abstract.

Sherer et al. "Coronary Artery Disease But Not Coronary Calcification Is Associated With Levels of Cardiolipin, β-2-Glycoprotein-I, and Oxidized LDL Antibodies", Cardiology, 95(1): 20-24, 2001. Abstract.

Stankusheva et al. "Ischemic Heart Disease-Clinical, Biochemical and Immunobiological Paralels", Vutr. Boles, 27(4): 88-91, 1988. Abstract.

Sevil et al. "Pharmacokinetic Analysis of β-Aminopropionitrile in Rabbits", Vet. Research, 27(2): 117-123, 1996. Abstract.

Harats et al. "β2-Glycoprotein I and Atherosclerosis", Current Opinion in Lipidology, 12: 543-546, 2001.

Wouters et al. "Understanding Hyperlipidemia and Atherosclerosis: Lessons From Genetically Modified Apoe and LDLR Mice", Clin. Chem. Lab. Med., 43(5): 470-479, 2005.

Maron et al. "Mucosal Administration of HSP65 Decreases Atherosclerosis and Inflammation in the Aortic Arch of LDL Receptor Deficient Mice", Immunology Letters, 73(2-3): 217, & 24th European Immunology Meeting of the European Federation of Immunological Societies (EFIS), Poznan, Poland, 2000. Abstract.

* cited by examiner

METHODS EMPLOYING AND COMPOSITIONS CONTAINING PLAQUE ASSOCIATED MOLECULES FOR PREVENTION AND TREATMENT OF ATHEROSCLEROSIS

RELATED PATENT APPLICATIONS

This application is a National Phase Application of PCT/IL02/00005 having International Filing Date Jan. 3, 2002, which claims priority from U.S. Provisional Patent Application No. 60/259,512 filed Jan. 4, 2001.

FIELD AND BACKGROUND OF THE INVENTION

The present invention relates to atheromatous plaque associated molecules for prevention and treatment of atherosclerosis and related disease and, more particularly, to methods and compositions employing plaque associated molecules effective in inducing mucosal tolerance and inhibiting inflammatory processes contributing to atheromatous vascular disease and sequalae.

Cardiovascular disease is a major health risk throughout the industrialized world. Atherosclerosis, the most prevalent of cardiovascular diseases, is the principal cause of heart attack, stroke, and gangrene of the extremities, and as such, the principal cause of death in the United States. Atherosclerosis is a complex disease involving many cell types and molecular factors (for a detailed review, see Ross, 1993, Nature 362: 801-809). The process, which occurs in response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when inflammatory cells such as monocyte-derived macrophages adhere to the vascular endothelial layer and transmigrate through to the sub-endothelial space. Elevated plasma LDL levels lead to lipid engorgement of the vessel walls, with adjacent endothelial cells producing oxidized low density lipoprotein (LDL). In addition, lipoprotein entrapment by the extracellular matrix leads to progressive oxidation of LDL by lipoxygenases, reactive oxygen species, peroxynitrite and/or myeloperoxidase as well as other oxidizing compounds. These oxidized forms of LDLs are then taken up in large amounts by vascular cells through scavenger receptors expressed on their surfaces.

Lipid-filled monocytes and smooth-muscle derived cells are called foam cells, and are the major constituent of the fatty streak. Interactions between foam cells and the endothelial and smooth muscle cells surrounding them produce a state of chronic local inflammation which can eventually lead to activation of endothelial cells, increased macrophage apoptosis, smooth muscle cell proliferation and migration, and the formation of a fibrous plaque (Hajjar, D P and Haberland, M E, J. Biol Chem 1997 Sep. 12; 272(37): 22975-78). Such plaques occlude the blood vessels concerned and thus restrict the flow of blood, resulting in ischemia, a condition characterized by a lack of oxygen supply in tissues of organs due to inadequate perfusion. When the involved arteries block the blood flow to the heart, a person is afflicted with a 'heart attack'; when the brain arteries occlude, the person experiences a stroke. When arteries to the limbs narrow, the result is severe pain, decreased physical mobility and possibly the need for amputation.

Oxidized LDL has been implicated in the pathogenesis of atherosclerosis and atherothrombosis, by it's action on monocytes and smooth muscle cells, and by inducing endothelial cell apoptosis, impairing anticoagulant balance in the endothelium. Oxidized LDL also inhibits anti-atherogenic HDL-associated breakdown of oxidized phospholipids (Mertens, A and Holvoet, P, FASEB J 2001 October; 15(12): 2073-84). This association is also supported by many studies demonstrating the presence of oxidized LDL in the plaques in various animal models of atherogenesis; the retardation of atherogenesis through inhibition of oxidation by pharmacological and/or genetic manipulations; and the promising results of some of the interventionaltrials with anti-oxidant vitamins (see, for example, Witztum J and Steinberg, D, Trends Cardiovasc Med 2001 April-May; 11(3-4):93-102 for a review of current literature). Indeed, oxidized LDL and malondialdehyde (MDA)-modified LDL have been recently proposed as accurate blood markers for $1^{st}$ and $2^{nd}$ stages of coronary artery disease (U.S. Pat. Nos. 6,309,888 to Holvoet et al and 6,255,070 to Witztum, et al).

Reduction of LDL oxidation and activity has been the target of a number of suggested clinical applications for treatment and prevention of cardiovascular disease. Bucala, et al (U.S. Pat. No. 5,869,534) discloses methods for the modulation of lipid peroxidation by reducing advanced glycosylation end product, lipid characteristic of age-, disease- and diabetes-related foam cell formation. Tang et al, at Incyte Pharmaceuticals, Inc. (U.S. Pat. No. 5,945,308) have disclosed the identification and proposed clinical application of a Human Oxidized LDL Receptor in the treatment of cardiovascular and autoimmune diseases and cancer.

Another abundant atherogenesis-related plaque component is Beta 2-Glycoprotein I. $Beta_2$-Glycoprotein I (Beta2GPI) is a 50-kDa molecule that acts as an anticoagulant in in-vitro assays. Although the exact role of Beta2GPI in atherogenesis has yet to be elucidated, several relevant properties have been observed: 1) it is able to bind negatively charged phospholipids or phospholipid-expressing cells (apoptotic cells, activated platelets); 2) it is able to bind to modified cellular surfaces, enhancing their clearance by scavenging macrophages (Chonn A, et al J Biol Chem 1995; 270: 25845-49; and Thiagarajan P, et al Arterioscler Thromb Vasc Biol 1999; 19:2807-11); and 3) it is an important target for binding of autoimmune antiphospholipid antibodies (aPLs). Beta2GPI has to undergo structural alteration in order to be recognized by aPLs. This alteration may be initiated, for example, by binding to negatively charged phospholipids or high binding plates, but also in vivo by binding apoptotic cells that express phophatidylserine.

Recent studies investigating the importance of anti Beta2GPI antibodies in promoting a procoagulant state have focused on the effects of these antibodies on cellular and protein components of the coagulation system (endothelial cells, platelets and macrophages; tissue factor and coagulation factors). These studies indicate that anti Beta2GPI antibodies prevent the deactivation of platelets, sustaining their phagocytic clearance; interact with late endosomes of human endothelial cells; and suppress the inhibitory activity of the tissue factor pathway inhibitor. This association with coagulation events is consistent with Beta2GPIs proposed function in the prothrombotic antiphospholipid syndrome (APLS). Both U.S. Pat. Nos. 5,998,223 and 5,344,758 (to Matsuura, et al and Krilis, et al, respectively) disclose the application of anti Beta2GPI antibodies, some to cryptic epitopes, for diagnostics in APLS and SLE. However, no therapeutic applications are disclosed by the authors.

A third important plaque-related component associated with atherogenesis is the 60/65 kDa heat shock protein (HSP). This mitochondrial protein is a member of the HSP family, which constitutes nearly 24 proteins displaying high degree of sequence homologies between different species. These proteins, as their name implies, are expressed in response to stresses including exposure to free radicals, heat, mechanical shear stress, infections and cytokines, and protect against unfolding and denaturation of cellular proteins. This has led to their designation as molecular 'chaperones'. However, HSP function may have undesired consequences, since over expression of HSPs may, under certain conditions promote an autoimmune reaction with resultant tissue damage. The mechanisms responsible for the HSP immune mediated damage are as yet unclear: it is presumed that cryptic, "non-self" neo-epitopes are exposed following their upregulation. Alternatively, it was suggested that cross-reaction exists between self-HSP and 'foreign' HSP epitopes introduced following infections which may trigger a pathological, autoimmune response against native HSP. Support for the involvement of HSP in autoimmunity is provided by studies documenting enhanced autoantibody as well as cellular response to HSP 60/65 in several autoimmune diseases (Schoenfeld, Y et al Autoimmunity 2000 September; 15(2): 199-202; U.S. Pat. No. 6,130,059 to Covacci, et al; and Gromadza G, et al Cerebrovascul Dis 2001, October; 12(3): 235-39). The link between HSP 65 and atherosclerosis was initially recognized by George Wick's group, who found that normocholesterolemic rabbits immunized with different antigens developed atherosclerosis, provided the preparation used for immunization contained complete Freund's adjuvant (CFA)(Xu, Q, et al Arterioscler Thromb 1992;12:789-99). Since the major constituent of CFA is heat killed mycobacterium tuberculosis, the principal component of which is the HSP-65, they reasoned that the immune response towards this component led to the development of atherosclerosis. This was confirmed when these authors demonstrated that immunization of animals with HSP 65 produced pronounced atherosclerosis, and that T cells from experimentally atherosclerotic rabbits overexpressed HSP-65, indicating a localized immune reaction restricted to the stressed arterial vessel. The importance of endogenous HSP-65 in atherogenesis was further demonstrated by the acceleration of fatty streak formation following HSP-65 (or *Mycobacterium tuberculosis*) immunization of naïve mice (George J, et al Arterioscler Thromb Vasc Biol 1999; 19:505-10;).

Involvement of humoral immune mechanisms in response to HSP-65 were observed in atherosclerosis: a marked correlation has been found between high levels of anti-HSP65 antibodies and the extent of sonographically estimated carotid narrowing in a screen of healthy individuals (Xu Q. et al Lancet 1993; 341: 255-9; Xu Q. et al Circulation 1999; 100(11): 1169-74). In addition, in-vitro experiments with cultured endothelial cells have demonstrated the concentration and time dependent induction of endothelial cell adhesion to monocytes and granulocytes following incubation with HSP65.

The association of HSP 65 with atherogenesis has led to a number of proposed therapeutic applications. Observing that immune reactivity to HSP 65 correlated with both microbial (e.g. *H. pylori*) infection and atherosclerosis, Bernie et al (Eur Heart J 1998; 19:366-7) proposed antibiotic therapy for reduction of infection and anti-HSP antibodies. Similarly, Covacci, et al (U.S. Pat. No. 6,130,059) disclosed the use of *H. pylori* HSPs, and related peptides, for diagnostic and therapeutic applications in atherosclerosis.

Atherosclerosis and Autoimmune Disease

Because of the presumed role of the excessive inflammatory-fibroproliferative response in atherosclerosis and ischemia, a growing number of researchers have attempted to define an autoimmune component of vascular injury. In autoimmune diseases the immune system recognizes and attacks normally non-antigenic body components (autoantigens), in addition to attacking invading foreign antigens. The autoimmune diseases are classified as auto-(or self-) antibody mediated or cell mediated diseases. Typical autoantibody mediated autoimmune diseases are myasthenia gravis and idiopathic thrombocytopenic purpura (ITP), while typical cell mediated diseases are Hashimoto's thyroiditis and type I (Juvenile) Diabetes.

The recognition that immune mediated processes prevail within atherosclerotic lesions stems from the consistent observation of lymphocytes and macrophages in the earliest stages, namely the fatty streaks. These lymphocytes, which include a predominant population of CD4+ cells (the remainder being CD8+ cells) were found to be more abundant than macrophages in early lesions, as compared with the more advanced lesions, in which this ratio tends to reverse. These findings posed questions as to whether they reflect a primary immune sensitization to a possible antigen or alternatively, result from previously induced local tissue damage. Regardless of the factors responsible for the recruitment of these inflammatory cells to the early plaque, they seem to exhibit an activated state manifested by concomitant expression of MHC class II HLA-DR and interleukin (IL) receptor as well as leukocyte common antigen (CD45R0) and the very late antigen 1 (VLA-1) integrin. Thus, the inflammatory reaction of the early stages of the atherosclerotic lesion may be either the primary initiating event leading to the production of various cytokines by the local cells (i.e endothelial cells, macrophages, smooth muscle cells and inflammatory cells), or one form of the immune system's response to the hazardous process. Some of the cytokines which have been shown to be upregulated by the resident cells include TNF-$\alpha$, IL-1, IL-2, IL-6, IL-8, IFN-$\gamma$ and monocyte chemoattractant peptide-1 (MCP-1). Platelet derived growth factor (PDGF) and insulin-like growth factor (ILGF) which are expressed by all cellular constituents within atherosclerotic plaques have also been shown to be overexpressed, thus possibly intensifying the preexisting inflammatory reaction by a co-stimulatory support in the form of a mitogenic and chemotactic factor. Recently, Uyemura et al. (J Clin Invest 1996; 97: 2130-2138) have elucidated type 1 T-cell cytokine pattern in human atherosclerotic lesions exemplified by a strong expression of IFN-$\gamma$ but not IL-4 mRNA in comparison with normal arteries. Furthermore, IL-12—a T-cell growth factor produced primarily by activated monocytes and a selective inducer of Th1 cytokine pattern, was found to be overexpressed within lesions as manifested by the abundance of its major heterodimer form p70 and p40 (its dominant inducible protein) mRNA.

Similar to the strong evidence for the dominance of the cellular immune system within the atherosclerotic plaque, there is also ample data supporting the involvement of the local humoral immune system. Thus, deposition of immunoglobulins and complement components has been shown in the plaques in addition to the enhanced expression of the C3b and C3Bi receptors in resident macrophages.

Valuable clues with regard to the contribution of immune mediated inflammation to the progression of atherosclerosis come from animal models. Immunocompromised mice (class I MHC deficient) tend to develop accelerated atherosclerosis as compared with immune competent mice. Additionally, treatment of C57BL/6 mice (Emeson E E and Shen M L Am J Pathol 1993; 142: 1906-1915) and New-Zealand White rabbits (Roselaar S E, et al J Clin Invest 1995; 96: 1389-1394) with cyclosporin A, a potent suppressor of IL-2 transcription resulted in a significantly enhanced atherosclerosis under "normal" lipoprotein "burden". These latter studies may provide insight into the possible roles of the immune system in counteracting the self-perpetuating inflammatory process within the atherosclerotic plaque.

Atherosclerosis is not a classical autoimmune disease, although some of its manifestations such as the production of the plaque that obstructs the vasculature may be related to aberrant immune responsiveness. In classical autoimmune disease, one can often define very clearly the sensitizing autoantigen attacked by the immune system and the component(s) of the immune system which recognize the autoantigen (humoral, i.e. autoantibody or cellular, i.e. lymphocytes). Above all, one can show that by passive transfer of these components of the immune system the disease can be induced in healthy animals, or in the case of humans the disease may be transferred from a sick pregnant mother to her offspring. Many of the above are not prevailing in atherosclerosis. In addition, the disease definitely has common risk factors such as hypertension, diabetes, lack of physical activity, smoking and others, the disease affects elderly people and has a different genetic preponderance than in classical autoimmune diseases.

Treatment of inflammatory disease may be directed towards suppression or reversal of general and/or disease-specific immune reactivity. Thus Aiello, for example (U.S. Pat. Nos. 6,034,102 and 6,114,395) discloses the use of estrogen-like compounds for treatment and prevention of atherosclerosis and atherosclerotic lesion progression by inhibition of inflammatory cell recruitment. Similarly, Medford et al (U.S. Pat. No. 5,846,959) disclose methods for the prevention of formation of oxidized PUFA, for treatment of cardiovascular and non-cardiovascular inflammatory diseases mediated by the cellular adhesion molecule VCAM-1. Furthermore, Falb (U.S. Pat. No. 6,156,500) designates a number of cell signaling and adhesion molecules abundant in atherosclerotic plaque and disease as potential targets of anti-inflammatory therapies.

Since oxidized LDL, Beta2GPI and HSP 65 have been clearly implicated in the pathogenesis of atherosclerosis (see above), the contribution of these prominent plaque components to autoimmunity in atheromatous disease processes has been investigated.

Immune Responsiveness to Plaque Associated Molecules

It is known that Ox LDL is chemotactic for T-cells and monocytes. Ox LDL and its byproducts are also known to induce the expression of factors such as monocyte chemotactic factor 1, secretion of colony stimulating factor and platelet activating properties, all of which are potent growth stimulants. The active involvement of the cellular immune response in atherosclerosis has recently been substantiated (Stemme S, et al, Proc Natl Acad Sci USA 1995; 92: 3893-97), who isolated CD4+ within plaques clones responding to Ox LDL as stimuli. The clones corresponding to Ox LDL (4 out of 27) produced principally interferon-γ rather than IL-4. It remains to be seen whether the above T-cell clones represent mere contact with the cellular immune system with the inciting strong immunogen (Ox LDL) or that this reaction provides means of combating the apparently indolent atherosclerotic process.

The data regarding the involvement of the humoral mechanisms and their meaning are much more controversial. One recent study reported increased levels of antibodies against MDA-LDL, a metabolite of LDL oxidation, in women suffering from heart disease and/or diabetes (Dotevall, et al., Clin Sci 2001 November; 101(5): 523-31). Other investigators have demonstrated antibodies recognizing multiple epitopes on the oxidized LDL, representing immune reactivity to the lipid and apolipoprotein components (Steinerova A, et al., Physiol Res 2001;50(2): 131-41) in atherosclerosis and other diseases, such as diabetes, renovascular syndrome, uremia, rheumatic fever and lupus erythematosus. Several reports have associated increased levels of antibodies to Ox LDL with the progression of atherosclerosis (expressed by the degree of carotid stenosis, severity of peripheral vascular disease etc.). Most recently, Sherer et al (Cardiology 2001;95(1):20-4) demonstrated elevated levels of antibodies to cardiolipin, β-2GPI and oxLDL, but not phosphatidylcholine or endothelial cells in coronary heart disease. Thus, there seems to be a consensus as to the presence of anti-plaque-component antibodies in the form of immune complexes within atherosclerotic plaque.

Antibodies to Ox LDL have been implicated in both normal and pathological lipoprotein metabolism. Thus, it is known that immune complexes of Ox LDL and its corresponding antibodies are taken up more efficiently by macrophages in suspension as compared with Ox LDL. No conclusions can be drawn from this consistent finding on the pathogenesis of atherosclerosis since the question of whether the accelerated uptake of Ox LDL by the macrophages is beneficial or deleterious has not yet been resolved.

Important data as to the significance of the humoral immune system in atherogenesis comes from animal models: hyperimmunization of LDL-receptor deficient rabbits with homologous oxidized LDL, resulted in the production of high levels of anti-Ox LDL antibodies and was associated with a significant reduction in the extent of atherosclerotic lesions. Likewise, a decrease in plaque formation followed the immunization of rabbits with cholesterol rich liposomes and stimulation of production of anti-cholesterol antibodies; however, this effect was accompanied by a undesirable 35% reduction in very low density lipoprotein cholesterol levels.

Regarding the immunogenicity of Beta2GPI, it has been shown that Beta2GPI serves as a target antigen for an immune-mediated attack, influencing the progression of atherosclerosis in humans and mice. George J et al. immunized LDL-receptor deficient mice with Beta2GPI, producing a pronounced humoral immune response to human Beta2GPI, and larger early atherosclerotic lesions in comparison with controls (George J, et al Circulation 1998; 15:1108-15). Afek A, et al obtained similar results in atherosclerosis-prone apolipoprotein-E-knockout mice immunized once with human Beta2GPI and fed a high fat diet for 5 weeks (Afek A et al. Pathobiology 1999;67:19-25).

Further, although immune reactivity to Beta2GPI in humans with the prothrombotic antiphospholipid syndrome has traditionally been attributed to the presence of autoantibodies to Beta2GPI, recent observations have indicated the importance of a cellular immune response to Beta2GPI. T-cells reactive with Beta2GPI have been demonstrated in the peripheral blood of patients with antiphospholipid syndrome. These T cells displayed a T-helper-1 phenotype (secreting the proinflammatory (and proatherogenic) cytokine interferon-) and were also capable of inducing tissue factor production (Visvanathan S., and McNiel H P. J Immunolog 1999; 162:6919-25). Taken together, the abundant data gathered to date regarding anti Beta2GPI (for review see Roubey R A, Curr Opinion Rheumatol 2000; 12:374-378), indicates that the immune response to this plaque related antigen may play a significant role in influencing the size and composition of atherosclerotic plaque.

Finally, there exists a significant dependency in the antigenicity, and pathogenicity of oxidized phospholipids and Beta2GPI. As mentioned above, some of the autoimmune epitopes associated with minimally modified LDL and Beta2GPI are cryptic. Kyobashi, et al (J Lipid Res 2001; 42:697-709), and Koike, et al (Ann Med 2000; 32:Suppl I 27-31) have identified a macrophage-activating oxLDL specific ligand present only with Beta2GPI-OxLDL complex formation. This ligand was recognized by APLS-specific autoantibodies. Thus, both the pathogenic role of oxidized LDL and other plaque components, and their importance as autoantigens in atherosclerosis, as well as other diseases, have been extensively demonstrated in laboratory and clinical studies.

Mucosal Tolerance in Treatment of Autoimmune Disease

Recently, new methods and pharmaceutical formulations have been found that are useful for treating autoimmune diseases (and related T-cell mediated inflammatory disorders such as allograft rejection and retroviral-associated neurological disease). These treatments induce tolerance, orally or mucosally, e.g. by inhalation, using as tolerizers autoantigens, bystander antigens, or disease-suppressive fragments or analogs of autoantigens or bystander antigens. Such treatments are described, for example, in U.S. Pat. No. 5,935,577 to Weiner et al. Autoantigens and bystander antigens are defined below (for a general review of mucosal tolerance see Nagler-Anderson, C., Crit Rev Immunol 2000; 20(2):103-20). Intravenous administration of autoantigens (and fragments thereof containing immunodominant epitopic regions of their molecules) has been found to induce immune suppression through a mechanism called clonal anergy. Clonal anergy causes deactivation of only immune attack T-cells specific to a particular antigen, the result being a significant reduction in the immune response to this antigen. Thus, the autoimmune response-promoting T-cells specific to an autoantigen, once anergized, no longer proliferate in response to that antigen. This reduction in proliferation also reduces the immune reactions responsible for autoimmune disease symptoms (such as neural tissue damage that is observed in multiple sclerosis; MS). There is also evidence that oral administration of autoantigens (or immunodominant fragments) in a single dose and in substantially larger amounts than those that trigger "active suppression" may also induce tolerance through anergy (or clonal deletion).

A method of treatment has also been disclosed that proceeds by active suppression. Active suppression functions via a different mechanism from that of clonal anergy. This method, discussed extensively in PCT Application PCT/US93/01705, involves oral or mucosal administration of antigens specific to the tissue under autoimmune attack. These are called "bystander antigens". This treatment causes regulatory (suppressor) T-cells to be induced in the gut-associated lymphoid tissue (GALT), or bronchial associated lymphoid tissue (BALT), or most generally, mucosa associated lymphoid tissue (MALT) (MALT includes GALT and BALT). These regulatory cells are released in the blood or lymphatic tissue and then migrate to the organ or tissue afflicted by the autoimmune disease and suppress autoimmune attack of the afflicted organ or tissue. The T-cells elicited by the bystander antigen (which recognize at least one antigenic determinant of the bystander antigen used to elicit them) are targeted to the locus of autoimmune attack where they mediate the local release of certain immunomodulatory factors and cytokines, such as transforming growth factor beta (TGF beta), interleukin-4 (IL-4), and/or interleukin-10 (IL-10). Of these, TGF-beta is an antigen-nonspecific immunosuppressive factor in that it suppresses immune attack regardless of the antigen that triggers the attack. (However, because oral or mucosal tolerization with a bystander antigen only causes the release of TGF-beta in the vicinity of autoimmune attack, no systemic immunosuppression ensues.) IL-4 and IL-10 are also antigen-nonspecific immunoregulatory cytokines. IL-4 in particular enhances (T helper 2) $Th_2$ response, i.e., acts on T-cell precursors and causes them to differentiate preferentially into $Th_2$ cells at the expense of $Th_1$ responses. IL-4 also indirectly inhibits $Th_1$ exacerbation. IL-10 is a direct inhibitor of $Th_1$ responses. After orally tolerizing mammals afflicted with autoimmune disease conditions with bystander antigens, increased levels of TGF-beta, IL-4 and IL-10 are observed at the locus of autoimmune attack (Chen, Y. et al., Science, 265:1237-1240, 1994). The bystander suppression mechanism has been confirmed by von Herreth et al., (J. Clin. Invest., 96:1324-1331, September 1996).

More recently, oral tolerance has been effectively applied in treatment of animal models of inflammatory bowel disease by feeding probiotic bacteria (Dunne, C, et al., Antonie Van Leeuwenhoek 1999 Jul-Nov; 76(1-4):279-92), autoimmune glomerulonephritis by feeding glomerular basement membrane (Reynolds, J. et al., J Am Soc Nephrol 2001 January; 12(1): 61-70) experimental allergic encephalomyelitis (EAE, which is the equivalent of multiple sclerosis or MS), by feeding myelin basic protein (MBP), adjuvant arthritis and collagen arthritis, by feeding a subject with collagen and HSP-65, respectively. A Boston based company called Autoimmune has carried out several human experiments for preventing diabetes, multiple sclerosis, rheumatoid arthritis and uveitis. The results of the clinical trials have been less impressive than the animal experiments, however there has been some success with the prevention of arthritis.

Oral tolerance to autoantigens found in atherosclerotic plaque lesions has also been investigated. Study of the epitopes recognized by T-cells and Ig titers in clinical and experimental models of atherosclerosis indicated three candidate antigens for suppression of inflammation in atheromatous lesions: oxidized LDL, the stress-related heat shock protein HSP 65 and the cardiolipin binding protein beta 2GP 1. U.S. patent application Ser. No. 09/806,400 to Shoenfeld et al (filed Sep. 30, 1999), which is incorporated herein in its entirety, discloses the reduction by approximately 30% of atherogenesis in the arteries of genetically susceptible LDL receptor deficient mice (LDL-RD) fed oxidized human LDL. Although significant inhibition of atherogenesis was achieved, presumably via oral tolerance, no identification of specific lipid antigens or immunogenic LDL components was made. Another obstacle encountered was the inherent instability of the orally fed antigen in vivo, due to digestive breakdown, and uptake of oxidized LDL by the liver and cellular immune mechanisms. It is plausible that a mucosal route of administration other than feeding (oral) would have provided tolerance of greater efficiency.

The induction of immune tolerance and subsequent prevention or inhibition of autoimmune inflammatory processes has been demonstrated using exposure to suppressive antigens via mucosal sites other than the gut. The membranous tissue around the eyes, the middle ear, the respiratory and other mucosa, and especially the mucosa of the nasal cavity, like the gut, are exposed to many invading as well as self-antigens and possess mechanisms for immune reactivity. Thus, Rossi, et al (Scand J Immunol 1999 August; 50(2):177-82) found that nasal administration of gliadin was as effective as intravenous administration in downregulating the immune response to the antigen in a mouse model of celiac disease. Similarly, nasal exposure to acetylcholine receptor antigen was more effective than oral exposure in delaying and reducing muscle weakness and specific lymphocyte proliferation in a mouse model of myasthenia gravis (Shi, FD. et al, J Immunol 1999 May 15; 162 (10): 5757-63). Therefore, immunogenic compounds intended for mucosal as well as intravenous or intraperitoneal administration should be adaptable to nasal and other membranous routes of administration.

Thus, there is clearly a need for novel methods of employing, and compositions of plaque associated molecules capable of superior tolerizing immunogenicity in mucosal, especially nasal, administration.

SUMMARY OF THE INVENTION

According to one aspect of the present invention there is provided a pharmaceutical composition for prevention and/or treatment of atherosclerosis, cardiovascular disease, cerebrovascular disease, peripheral vascular disease, stenosis, restenosis and/or in-stent-stenosis in a subject in need thereof, comprising, as an active ingredient, a therapeutically effective amount of at least an antigenic portion of at least one plaque associated molecule, or pharmaceutical salts thereof, the composition further comprising a pharmaceutically acceptable carrier, the pharmaceutical composition being designed for mucosal administration.

According to an additional aspect of the present invention there is provided an assay for determining the effect of mucosal administration of plaque components on atherosclerosis-related disease or condition, the assay effected by mucosally administering to a subject having an atherosclerosis-related disease or condition at least an antigenic portion of at least one plaque associated molecule and assessing at least one indicator of atherogenesis in the subject to thereby determine the effect of mucosal administration of the at least an antigenic portion of the at least one plaque associated molecule on the atherosclerosis-related disease or condition.

According to yet another aspect of the present invention there is provided a method of prevention and/or treatment of atherosclerosis, cardiovascular disease, cerebrovascular disease, peripheral vascular disease, stenosis, restenosis and/or in-stent-stenosis in a subject in need thereof, the method comprising mucosally administering a therapeutically effective amount of at least an antigenic portion of at least one plaque associated molecule to the subject.

According to further features in preferred embodiments of the invention described below, the plaque associated molecule is selected from the group consisting of oxidized LDL, Beta2GPI, HSP and derivatives thereof.

According to still further features in preferred embodiments of the invention described below, the antigenic portion of at least one plaque associated molecule is a naturally occurring molecule or a synthetic molecule.

According to further features in preferred embodiments of the invention described below, the pharmaceutical composition is designed for nasal, respiratory, otic and/or conjuctival administration.

According to yet further features in preferred embodiments of the invention described below the at least an antigenic portion of the at least one plaque associated molecule is selected so as to reduce immune reactivity to plaque components in said subject.

According to further features in preferred embodiments of the invention described below, the pharmaceutical composition is packaged and identified for use in the prevention and/or treatment of at least one disorder selected from the group consisting of atherosclerosis, cardiovascular disease, cerebrovascular disease, peripheral vascular disease, stenosis, restenosis and/or in-stent-stenosis.

According to further features in preferred embodiments of the invention described below the pharmaceutical composition further comprises a therapeutically effective amount of at least one additional compound selected from the group consisting of HMGCoA reductase inhibitors (statins), mucosal adjuvants, corticosteroids, anti-inflammatory compounds, analgesics, growth factors, toxins, and additional tolerizing antigens.

The present invention successfully addresses the shortcomings of the presently known configurations by providing a novel method of inducing superior immune tolerance by mucosal administration of plaque associated molecules, thereby inhibiting atheroslerosis and other plaque related diseases.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

Control mice were exposed intranasally to an identical volume (10 µl) of bovine serum albumin, 10 µg/mouse (BSA)(n=14), or sham exposure to PBS (PBS)(n=14). All mice received the atherogenic "Western" diet following last exposure. Atherogenesis is expressed as the area of atheromatous lesions in the aortic sinus 5 weeks after the last nasal exposure.

Figure 3:
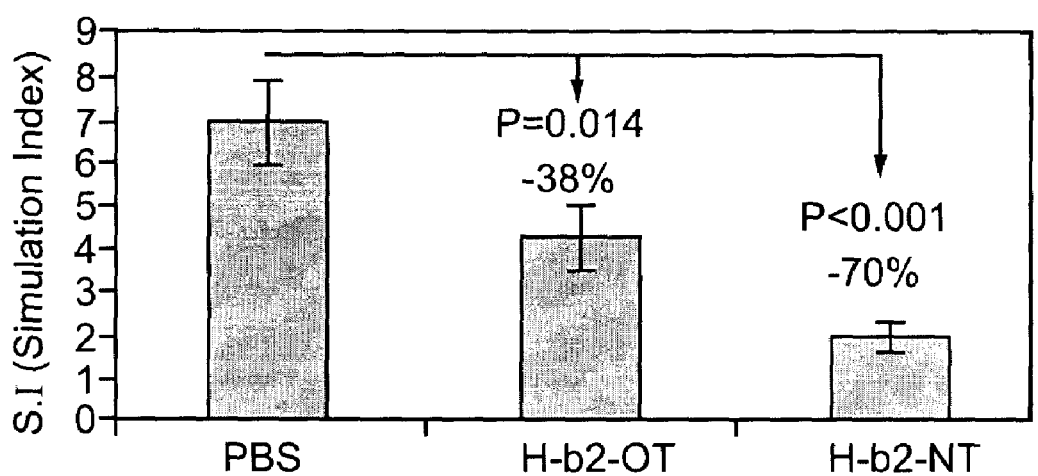

FIG. 3 illustrates superior suppression of immune reactivity to atheroslerotic plaque antigens induced by nasal exposure to human Beta2GPI. 5 week old male apo-E deficient mice were exposed intranasally to 10 µg/mouse human Beta2GPI (H-b2-nt)(n=3); or alternately fed, by gavage, with 100 µg/mouse human Beta2GPI (H-b2-ot) (n=3) in 0.2 ml PBS; or fed PBS alone (PBS)(n=3) every other day for 5 days. One week following the last feeding the mice were sensitized with a single subcutaneous injection of 10 µg/mouse human Beta2GPI in 0.1 ml volume. Ten days later T-cells from inguinal lymph node were prepared as described in Materials and Methods section that follows, and exposed to the sensitizing human Beta2GPI antigen for in-vitro assessment of proliferation. Proliferation, indicating immune reactivity, is expressed as the ratio between incorporation of labeled thymidine into the T-cell's DNA in the presence and absence of human Beta2GPI antigen (stimulation index, S.I.).

DESCRIPTION OF THE PREFERRED EMBODIMENTS

The present invention is of methods and compositions employing plaque associated molecules effective in inducing mucosal tolerance to atheroma related antigens, thus inhibiting inflammatory processes contributing to atheromatous vascular disease and sequalae.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Experimental and clinical evidence indicates a causative role for plaque associated antigens in the etiology of the excessive inflammatory response in atherosclerosis. Both cellular and humoral immune reactivity to the plaque associated molecules oxidized LDL, Beta2GPI and HSP 65 have been demonstrated, suggesting an important anti-oxidized LDL auto-immune component in atherogenesis. Thus, oxidized LDL, Beta2GPI and HSP 65, and components thereof, have been the targets of numerous therapies for prevention and treatment of heart disease, cerebral-vascular disease and peripheral vascular disease.

Prior art teaches the application of plaque associated antigens for detection and diagnosis of atherosclerosis and other plaque- and thrombosis related conditions. For example, Holvoet (U.S. Pat. No. 6,309,888) teaches the use of stage specific plaque associated antigens oxLDL and MDA-LDL for screening for Coronary Artery disease. Similarly, others (U.S. Pat. Nos. 5,998,223 and 5,344,758 to Matsuura, et al and Krilis, et al, respectively) have disclosed the use of anti beta-2GPI antibodies to screen for serum indicators of APLS, SLE and atherosclerosis. The above-mentioned disclosures propose diagnostic applications alone, and fail to recognize the therapeutic potential of these plaque associated molecules.

Although the role of immune response in the etiology and progression of atherosclerosis and other plaque related diseases remains controversial (see Meir, K, et al, International Atherosclerosis Soc. 2001 Commentary), many immune-based therapies have been proposed for atherosclerosis. General methods of reducing immune response in inflammatory and hyperreactive conditions are taught in, for example U.S. Pat. Nos. 6,277,969; 5,698,195 and 5,656,272 to Le at al, and 6,224,902 to Alving, et al, International Patent Application Nos. 001 001 2514 to Shurkovitz et al and 20010051156 A1 to Zeng. However, the proposed reduction or removal of mediators of immune reactivity, such as cytokines, tumor necrosis factor (TNF) and other pathogenic factors requires ongoing costly and potentially dangerous methods such as immunoadsorption of blood and prolonged anti-cytokine administration. Furthermore, no application to treatment of atherosclerosis or plaque-related disease is disclosed.

Specific immunotherapy with plaque associated antigens has also been proposed. Bumol, et al, Calenoff, et al and Takano, et al (U.S. Pat. Nos. 5,196,324; 6,025,477 and 5,110,738, respectively) disclose the use of crude, poorly defined fractionated plaque preparations for immunization, monoclonal Ab preparation, diagnosis and treatment of atherosclerosis. These antigens, protein and lipid fractions of atheromatous tissue, are poorly defined, impractical for therapeutic use, and potentially hazardous in prolonged treatment.

Prior art teaches immunotherapy directed against oxidized LDL for treatment and prevention of atherosclerosis. U.S. Pat. No. 6,225,070 to Witztum, et al discloses the use of mAb to oxidized LDL for inhibition of oxidized LDL binding to macrophages and foam cell formation. Similarly, McGregor, et al (International Patent Application EP1162458 A1) disclose methods for specific modulation of oxidized LDL uptake and transport by macrophages. U.S. Pat. Nos. 5,733,524 and 5,733,933 to Bucala, et al disclose the reduction of specific anti-oxidized LDL immune response by reduction of Advanced Glycosylation End product lipids (AGE-lipids). None of the proposed therapies teach active immunization against oxidized LDL, and require prolonged therapy regimens.

Zhou, et al (Arterioscler Thromb Vasc Biol, 2001;21:108) achieved a significant reduction in early plaque formation in mice following footpad immunization with homogenized plaque or homologous MDA LDL. Palinski et al (PNAS USA 1995;92:821-25) produced similar levels of protection in rabbits immunized with oxidized LDL. However, application of conventional immunization techniques to oxidized LDL is problematic, since the adjuvant preparations required for immunization and boosters have produced accelerated plaque formation in similar regimen of immunization. Furthermore, relatively high doses (100 µgram/mouse/injection) of plaque antigen were required for immunity. Mucosal administration and induction of tolerance were not mentioned.

Immune therapy with other plaque antigens has also been proposed. Recent animal and in-vitro studies with Beta2GPI (see George J, et al Rheum Dis Clin North Am 2001;27: 603-10; Brey, et al Stroke 2001;32:1701-06; Kyobashi, et al J Lipid Res 2001;42:697-709; Koike T., et al Ann Med 2000;32, Suppl. I:27-31 and Cabral A R et al Am J Med 1996;101:472-81) have demonstrated the association of Beta2GPI with stroke, APLS, atherosclerosis and myocardial infarction. Although cryptic epitopes of the protein were clearly implicated in humoral and cellular immune response to oxidized LDL, none of the abovementioned studies demonstrated protective immunity with the protein. Similarly, studies with HSP 65 (Birnie D H Eur Heart J 1998;19:366-67; Xu Q, et al Circulation 1999;100:1169-74; and Gromadzka G, et al Cerebrovasc Dis 2001;12:235-39) have implicated this plaque associated antigen in stroke and heart disease, suggesting that humoral immunity may be a triggering factor.

The complexity of plaque antigen immunity in atherosclerosis was demonstrated by Schoenfeld Y, et al (Autoimmunity 2000;15:199-202) who immunized LDL-receptor deficient (KO) mice with both HSP 65 and Beta2GPI protein antigens, producing strong cellular and humoral responses, and enhanced plaque formation. Similar increased atherogenesis was observed with passive transfer of plaque antigen activated lymphocytes. None of the above mentioned studies demonstrated inhibition of atherogenic processes by immune tolerance.

Suppression of immune response to autoantigens in atherosclerosis and related disease has been recently investigated. Victoria et al (U.S. Pat. Nos. 6,207,160 and 5,844,409) discloses specific non-immunogenic Beta2GPI peptides lacking T cell epitopes for reducing antibody binding of immune cells and inducing B-cell tolerance in APLS, SLE and other diseases. However, no actual protection was demonstrated, and the disclosures emphasize the diagnostic use of the non immunogenic peptides. George J, et al (Atherosclerosis 1998;138:147-52) demonstrated the feasibility of immune suppression by hyperimmunization with MDA LDL and reduction of atherogenesis in mice. However, impractically large doses of antigen were required, and the paradoxical response to immunization with plaque antigens obviates the clinical efficacy of such therapy. Furthermore, none of the abovementioned studies disclose induction of mucosal tolerance for treatment of atherosclerosis.

Oral and mucosal tolerance for suppression and prevention of inflammatory conditions is well known in the art. Examples of candidate conditions, antigens and modes of therapy, can be found, for example in U.S. Pat. Nos. 5,935,577; 5,397,771; 4,690,683 to Weiner et al., and International Pat Nos. EP 0886471 A1 and WO 01821951 to Haas, et al. U.S. patent application Ser. No. 09/806,400 to Shoenfeld et al filed Sep. 30, 1999, which is incorporated herein in its entirety, teaches the oral administration of plaque associated antigens for the induction of tolerance in LDL receptor deficient mice. Measuring arterial fatty streak lesion density, the inventors demonstrated that oral administration of oxidized LDL, Beta2GPI and HSP 65 derived from animal sources were each able to produce approximately 30% reduction in atherogenesis. Typically, however, oral administration of antigens presents numerous obstacles to achieving tolerance and accurate dosing: the antigens are acted upon by digestion, altering both concentrations and molecular structure prior to their presentation to the lymphatic tissue of the Peyer's patches. Furthermore, the authors failed to investigate the efficacy of other routes of administration for induction of tolerance, such as mucosal and nasal tolerance. As the above mentioned disclosures clearly demonstrate, the parameters for induction of oral and mucosal tolerance cannot be deduced from antigenic activity in conventional immunization, or even in-vitro results, and must result from extensive empirical experimentation. Indeed, many studies have demonstrated the complexities inherent in manipulating the "balance between reacting and nonreacting" in the immune system. Zivny, et al (Clin Immunol 2001; 101:150-68) clearly state that "In general, the response to one (tolerance inducing) antigen could not necessarily predict the response to another". Likewise, Hannihen et al (Diabetes 2001;50:771-75) observed that oral, nasal and respiratory administration of antigens caused appearance of disease symptoms (diabetes), rather than inducing tolerance. Similar inconsistencies in mucosal tolerance have been reported by Fujihashi et al (Acta Odontol Scand 2001;59:301-08), Jiang H R et al (Br J Ophthalmol 2001;85:739-44). Problems in mucosal vaccination strategies have been recently reviewed (Ogra P L, et al, Clin Microbiol Rev 2001;14:430-45; Chen H et al, J Control Release 2000;67:117-28; and Lehner T et al, J Infect Dis 1999;179 Suppl 3:S489-92).

While reducing the present invention to practice, the present inventors have uncovered that nasal administration of plaque associated molecules results in the induction of mucosal tolerance, suppression of anti-plaque related antigen immune reactivity and protection from atherosclerosis. Mucosal tolerance is advantageous for its greater ease of application, accuracy of dosage and greatly reduced incidence of alteration of the tolerizing molecule by digestive and metabolic processes (especially in non-oral routes of administration). These advantages provide superior protection from atherogenic processes, improved patient compliance and reduced cost of therapy.

Thus, according to one aspect of the present invention there is provided a method of inducing immune tolerance to plaque associated molecules in a subject such as a human being.

The method, according to this aspect of the present invention is effected by administering to a subject (e.g., a human) a therapeutically effective amount of an antigenic portion of at least one plaque associated molecule.

As used herein, the phrase "mucosal administration" is defined as application of any and all compounds and/or compositions to mucosal membranes having component or components of the mucosal associated lymphatic tissue. Non-limiting examples of mucosal administration are buccal, intranasal, otic (middle ear), conjunctival, vaginal, rectal, etc. Mucosal administration excludes, for example, intravenous, subcutaneous and epidural administration.

As used herein, the phrase "plaque associated molecules" is defined as any and all protein, carbohydrate, lipid and nucleic acid molecules, portions thereof (antigenic portions), their derivatives, or combinations thereof physically or functionally related to the etiology, pathogenesis, symptomatology and/or treatment of a plaque related condition or disease. Such molecules may be, for example, plaque components such as oxidized LDL, foam cell components, etc, but may also include humoral and cellular entities, such as antibodies, cytokines, growth factors and T cell receptors.

As used herein, the phrase "antigenic portion" refers to a portion of a molecule capable of eliciting an immune response. For example, in cases where the molecule is a protein (e.g., HSP 65, Beta2GPI) such a portion can include a stretch of 6-8 amino acids that constitute an antigenic epitope. Methods for predicting antigenic portions are well known in the art, for example, DNASTAR'S PROTEAN sequence analysis and prediction module (DNAStar, Madison, Wis.). As such determining antigenic portions of plaque associated molecules suitable for use with the present invention is well within the capabilities of an ordinarily skilled artisan.

Plaque associated molecules (as well as fragments, analogs, portions and derivatives thereof) can be purified from natural sources (the tissue or organ where they normally occur) and can also be obtained using recombinant DNA technology, in bacterial, yeast, insect (e.g. baculovirus) and mammalian cells using techniques well-known to those of ordinary skill in the art. Amino acid sequences for many potential and actual plaque associated molecules are known, for example: human Beta2GPI (Accession No AAB21330 to Matsuura, et al), HSP65 (Accession No. AF65546 to Oliviera, et al) and human macrophage LDL scavenger receptor (Accession No. XP_008489 to NCBI Annotation Project).

Immune tolerance established using the present methodology can be used in the prevention and/or treatment of disorders associated with plaque formation, including but not limited to atherosclerosis, atherosclerotic cardiovascular disease, cerebrovascular disease, peripheral vascular disease, stenosis, restenosis and in-stent-stenosis. Some non-limiting examples of atherosclerotic cardiovascular disease are myocardial infarction, coronary arterial disease, acute coronary syndromes, congestive heart failure, angina pectoris and myocardial ischemia. Some non-limiting examples of peripheral vascular disease are gangrene, diabetic vasculopathy, ischemic bowel disease, thrombosis, diabetic retinopathy and diabetic nephropathy. Non-limiting examples of cerebrovascular disease are stroke, cerebrovascular inflammation, cerebral hemorrhage and vertebral arterial insufficiency. Stenosis is occlusive disease of the vasculature, commonly caused by atheromatous plaque and enhanced platelet activity, most critically affecting the coronary vasculature. Restenosis is the progressive re-occlusion often following reduction of occlusions in stenotic vasculature. In cases where patency of the vasculature requires the mechanical support of a stent, in-stent-stenosis may occur, re-occluding the treated vessel.

Several plaque associated molecules are suitable for use with the present method. Examples include, but are not limited to, modified lipids, phospholipids and lipoproteins, apolipoprotein-lipid complexes such as LDL-cardiolipin, specific epitopes of proteinaceous molecules such as HSP and Beta2GPI, foam cell surface antigens such as LDL receptor and smooth muscle components such as troponin.

According to a preferred embodiment of the present invention the plaque associated molecule(s) utilized by the method of the present invention is oxidized LDL, Beta2GPI, HSP 65 and/or derivatives thereof.

According to another preferred embodiment of the present invention, a combination of at least two of the abovementioned molecules is administered to the subject.

The method of the invention may be used for prevention and/or treatment of non-atherosclerosis related diseases. For example, phospholipids, phospholipid metabolites and HSP 65 have been clearly implicated in the pathogenesis, and therefore potential treatment of additional, non-atherosclerosis-related diseases. Such diseases and syndromes include oxidative stress of aging (Onorato J M, et al, Annal N Y Acad Sci 1998 Nov. 20;854:277-90), rheumatoid arthritis (RA)(Paimela L, et al. Ann Rheum Dis 1996 August;55(8): 558-9), juvenile rheumatoid arthritis (Savolainen A, et al, 1995;24(4):209-11), inflammatory bowel disease (IBD) (Sawai T, et al, Pediatr Surg Int 2001 May; 17(4):269-74), renal cancer (Noguchi S, et al, Biochem Biophys Res Commun 1992 Jan. 31;182(2):544-50), venous and arterial thromboses (Cabral A R, et al Am J Med 1996;101:472-81), Anti Phospholipid Syndrome (APLS or APS) (Koike T, et al Ann Med 2000;32 Suppl 1:27-31), Systemic Lupus Erythematosus (U.S. Pat. Nos. 5,344,758 and 6,207,160, to Krilis, et al and Victoria, et al, respectively). Thus, the method of the invention may be used for prevention and/or treatment of non-atherosclerosis related diseases such as aging, RA, juvenile RA, IBD, SLE, APLS, thrombosis and cancer.

The immune tolerance inducing molecules or molecule combinations described hereinabove can be administered per se, or in a pharmaceutical composition where they are mixed with suitable carriers or excipients.

As used herein a "pharmaceutical composition" refers to a preparation of one or more of the active ingredients described herein with other chemical components such as physiologically suitable carriers and excipients. The purpose of the pharmaceutical composition of the present invention is to facilitate mucosal administration of the immune tolerance inducing molecules to an organism.

Herein the term "active ingredient" refers to the at least an antigenic portion of the plaque associated molecules (e.g. oxidized LDL, HSP 65, and beta2GP-I) or combinations thereof which are accountable for the biological effect (immune tolerance).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of mucosal administration may, for example, include rectal, buccal, vaginal and especially transnasal, otic, conjunctival and respiratory (including intratracheal) application.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the mucosal route of administration chosen.

The active ingredients of the pharmaceutical composition may be formulated in aqueous solutions, preferably in physiologically compatible buffers such as Hank's solution, Ringer's solution, or physiological salt buffer. Penetrants appropriate to the barrier to be permeated may used in the formulation. Such penetrants are generally known in the art.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition of the present invention may be administered to the membranes of the eye, such as the conjuctiva. As such, the composition may be formulated in a liquid or semi-liquid composition, as described above, for application using for example, a drop applicator. Sterility may be ensured by sterilization methods known to one skilled in the art.

The pharmaceutical composition of the present invention may be formulated in rectal and vaginal compositions such as suppositories or retention enemas, using, e.g., conventional suppository bases such as cocoa butter or other glycerides.

The pharmaceutical composition of the present invention may be administered by inhalation. Examples of formulations for tolerizing agents that are administered by inhalation are provided in PCT/US90/07455, filed Dec. 17, 1990. The pharmaceutical formulations for administration by inhalation of the present invention may include, as optional ingredients, pharmaceutically acceptable carriers, diluents, solubilizing and emulsifying agents, and salts of the type that are well-known in the art. Examples of such substances include normal saline solutions, such as physiologically buffered saline solutions, and water.

The route of administration of tolerizing antigens according to this alternate embodiment of the present invention is in an aerosol or inhaled form.

The antigens can be administered as dry powder particles or as an atomized aqueous solution suspended in a carrier gas (e.g. air or $N_2$). Preferred aerosol pharmaceutical formulations may comprise for example, a physiologically-acceptable buffered saline solution containing between about 1 mg and about 300 mg of the antigens.

Dry aerosol in the form of finely divided solid particles of tolerizing antigens that are not dissolved or suspended in a liquid are also useful in the practice of the present invention. The tolerizing antigens may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the by-inhalation pharmaceutical formulations include water and physiologically-acceptable buffered saline solutions such as phosphate buffered saline solutions pH 7.0-8.0. Additional non-limiting examples of suitable carriers or diluents for use in by-inhalation pharmaceutical formulations or dosage forms of the present invention are disclosed in U.S. Pat. No. 5,935,577 to Weiner, et al.

The pharmaceutical formulations of the present invention may be administered in the form of an aerosol spray using for example, a nebulizer such as those described by Weiner, et al (U.S. Pat. No. 5,935,577). The aerosol material is inhaled by the subject to be treated.

Other systems of aerosol delivery, such as the pressurized metered dose inhaler (MDI) and the dry powder inhaler as disclosed in Newman, S. P. in Aerosols and the Lung, Clarke, S. W. and Davia, D. eds. pp. 197-224, Butterworths, London, England, 1984, can be used when practicing the present invention. Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

Pharmaceutical compositions suitable for use in context of the present invention include compositions wherein the active ingredients are contained in an amount effective to achieve the intended purpose. More specifically, a therapeutically effective amount means an amount of active ingredients effective to induce an immune response thus preventing, alleviating or ameliorating symptoms of a disorder (e.g., atherosclerosis).

Ascertaining the optimum regimen for administering the active ingredient(s) is determined in light of the information disclosed herein and well known information concerning administration of mucosally active antigens, and autoantigens. Routine variation of dosages, combinations, and duration of treatment is performed under circumstances wherein the severity of atheromatous development can be measured. Useful dosage and administration parameters are those that result in reduction in inflammatory reaction, including a decrease in number of autoreactive T-cells, or in the occurrence or severity of at least one clinical or histological symptom of the disease.

The pharmaceutical composition of the present invention can be formulated comprising a therapeutically effective amount of additional compound or compounds useful in treating or preventing plaque related disease. In one preferred embodiment the additional compounds are HMGCoA reductase inhibitors (statins), mucosal adjuvants (see, for example, U.S. Pat. No. 6,270,758 to Staats, et al), corticosteroids, anti-inflammatory compounds (see, for example U.S. Pat. No. 6,297,260 to Bandarage, et al), analgesics, growth factors, toxins and additional tolerizing agents. In addition, it will be appreciated that use of the methods and compositions of the present invention does not preclude the initiation or continuation of other therapies for the above-mentioned diseases or conditions, except where of specifically counterindicated.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

In further preferred embodiments of the present invention, cytokine and non-cytokine synergists can be conjoined in the treatment to enhance the effectiveness of mucosal tolerization with plaque associated molecules. Oral and parenteral use of other cytokine synergists (Type I interferons) has been described in PCT/US95/04120, filed Apr. 7, 1995. Administration of Th2 enhancing cytokines is described in PCT application no. PCT/US95/04512, filed Apr. 7, 1995. For example, IL-4 and IL-10 can be administered in the manner described in PCT/US95/04512.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingi, et al., 1975, in "The Pharmacological Basis of Therapeutics", Ch. 1 p.1).

Dosage amount and interval may be adjusted individually to provide mucosal levels of the active ingredient that are sufficient to induce tolerance. The "tolerizing dosage" will vary for each preparation, but can be estimated from in vitro data. Dosages necessary to achieve tolerizing dosage will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise an inhaler. The pack or inhaler may be accompanied by instructions for administration. The pack or inhaler may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that administration of the tolerizing compositions and methods of the present invention may be effected by additional non mucosal methods such as intradermal, subcutaneous and intraperitoneal application.

According to another aspect of the present invention, there is provided an assay for determining the effects of mucosal administration of plaque associated molecules on artherosclerosis related disease or condition, the assay effected by mucosally administering the plaque associated molecule or composition thereof to a subject having such a disease or condition, and assessing at least one indicator of atherogenesis or inflammation. In a preferred embodiment, the plaque associated molecule is oxidized LDL, beta-2-GPI, HSP and/or derivates thereof. In another embodiment at least an antigenic portion of at least one plaque associated molecule is administered mucosally, the plaque associated molecule being a naturally occurring or synthetic molecule.

Indicators of atherogenesis or inflammation that can be assessed in the context of the assay of the present invention are known to the art. Some non-limiting examples are histological methods such as fatty streak lesion count, and immunological methods such as Stimulation Index, as described herein in Examples section that follows. Progression of atherosclerosis can be assessed, for example, in atherosclerosis-prone mice maintained on an atherogenic diet (see, for example, George J, et al Circulation 1999;99: 2227-30). Inflammation can be assessed by cytological, immunological, biochemical, molecular and genetic techniques known in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include biochemical and immunological techniques. Such techniques are thoroughly explained in the literature. See, for example, "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; and "Methods in Enzymology" Vol. 1-317, Academic Press; Marshak et al., all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Animals: Apo-E deficient mice used in these experiments are from the atherosclerosis prone strain C57BL/6J-Apo-E$^{tm\ 1\ unc}$. Mice homozygous for the Apo-E$^{tm\ 1\ unc}$ mutations show a marked increase in total plasma cholesterol levels which is unaffected by age or sex. Fatty streaks in the proximal aorta are found at 3 months of age. The lesions increase with age and progress to lesions with less lipid but more elongated cells, typical of a more advanced stage of pre-atherosclerotic lesion.

Strain Development: The Apo-E$^{tm\ 1\ unc}$ mutant strain was developed in the laboratory of Dr. Nobuyo Maeda at University of North Carolina at Chapel Hill. The 129-derived E14Tg2a ES cell line was used. The plasmid used is designated as pNMC109 and the founder line is T-89. The C57BL/6J strain was produced by backcrossing the Apo-E$^{tm\ 1\ unc}$ mutation 10 times to C57BL/6J mice (11, 12).

The mice were maintained at the Sheba Hospital Animal Facility (Tel-Hashomer, Israel) on a 12-hour light/dark cycle, at 22-24° C. and fed a normal fat diet of laboratory chow (Purina Rodent Laboratory Chow No. 5001) containing 0.027% cholesterol, approximately 4.5% total fat, and water, ad libitum. "Western diet" (TD 96125, Harlan Teklad, 42% calories from fat, 43% from carbohydrates and 15% from protein) describes a standardized, high fat atherogenic diet.

Nasal Tolerance: Nasal tolerance was induced by intranasal administration of oxidized LDL, Beta2GPI or HSP65, in a total volume of 10 μl PBS. Intranasal administration was performed on mildly sedated mice (12-16 weeks old), each mouse receiving 3 doses of antigen per dose, in the indicated concentrations, every other day. Atherogenesis was induced by 5 weeks of a Western diet, initiated on the day following the last intranasal administration. Controls received equal amounts of BSA and/or PBS, as indicated, in an identical regimen. Plasma samples were obtained for assessment of cholesterol and triglyceride levels from all mice, and the mice were sacrificed for evaluation of atherosclerosis, as described hereinbelow, after 5 weeks Western diet.

Oral Tolerance: For comparison, oral tolerance to plaque associated molecules was induced by feeding 3 doses of antigen every other day (for a detailed account of induction of oral tolerance, see U.S. patent application Ser. No. 09/806,400 to Shoenfeld et al filed Sep. 30, 1999), in a similar regimen to the nasal tolerance.

Antigen Preparation

Beta2GPI: Human Beta2GPI was purified from the serum of a healthy adult as described by Gharavi, et al (J Clin Invest 1992;92: 1105-09).

Oxidized LDL: Human LDL (density=1.019-1.063 g/l) was prepared from Plasma of fasting individuals by preparative ultracentrifugation (50,000 rpm/min, 22 min), washing, dialysis against 150 mM EDTA, pH 7.4, filtration (0.22 μm pore size) to remove aggregation, and storage under nitrogen. LDL oxidation was performed by incubation of dialyzed, EDTA-free LDL with copper sulfate (10 μM) for 24 hours at 37° C. Lipoprotein oxidation was confirmed by analysis of thiobarbituric acid-reactive substances (TBARS), which measures malondialdehyde (MDA) equivalents.

HSP65: Recombinant mycobacterial HSP-65, prepared as described (Prohaszka Z et al, Int Immunol 1999; 11:1363-70) was kindly provided by Dr. M. Singh, Braunschweig, Germany.

Immunization: Subcutaneous immunization with human Beta2GPI: Human Beta2GPI was prepared from human plasma pool as described above. For immunization, human Beta2GPI was dissolved in PBS and mixed with equal volumes of Freund's incomplete adjuvant. Immunizations were performed by single subcutaneous injection of 10 μg antigen/mouse in 0.1 ml volume. Three days following the last mucosal administration of plaque associated molecules the mice received one immunization, and were sacrificed 10 days post immunization.

Cholesterol Level Determination: At the completion of the experiment, 1-1.5 ml of blood was obtained by cardiac puncture into vials containing EDTA, centrifuged to separate plasma. Total plasma cholesterol levels were determined using an automated enzymatic technique (Boehringer Mannheim, Germany).

FPLC Analysis: Fast Protein Liquid Chromatography analysis of cholesterol and lipid content of lipoproteins was performed using Superose 6 HR 10/30 column (Amersham Pharmacia Biotech, Inc, Peapack, N.J.) on a FPLC system (Pharmacia LKB. FRAC-200, Pharmacia, Peapack, N.J.). A minimum sample volume of 300 μl (blood pooled from 3 mice was diluted 1:2 and filtered before loading) was required in the sampling vial for the automatic sampler to completely fill the 200 μl sample loop. Fractions 10-40 were collected, each fraction contained 0.5 ml. A 250 μl sample from each fraction was mixed with freshly prepared cholesterol reagent or triglyceride reagent respectively, incubated for 5 minutes at 37° C. and assayed spectrophotometrically at 500 nm.

Assessment of Atherosclerosis: Quantification of atherosclerotic fatty streak lesions was done by calculating the lesion size in the aortic sinus as previously described (George J et al Circulation 1999;99:2227-30) and by calculating the lesion size in the aorta. Briefly, after perfusion with saline Tris EDTA, the heart and the aorta were removed from the animals and the peripheral fat cleaned carefully. The upper section of the heart was embedded in OCT medium (10.24% w/w polyvinyl alcohol; 4.26% w/w polyethylene glycol; 85.50% w/w nonreactive ingredients) and frozen. Every other section (10 μm thick) throughout the aortic sinus (400 μm) was taken for analysis. The distal portion of the aortic sinus was recognized by the three valve cusps that are the junctions of the aorta to the heart. Sections were evaluated for fatty streak lesions after staining with oil-red O. Lesion areas per section were scored on a grid by an observer counting unidentified, numbered specimens. The aorta was dissected from the heart and surrounding adventitious tissue was removed. Fixation of the aorta and Sudan staining of the vessels were performed as previously described (George J et al Circulation 1999;99:2227-30).

Proliferation assays: Mice were exposed to the tested antigen as described for assessment of atherosclerosis, and then immunized (one to three days following the last exposure) subcutaneously with 10 μg Beta2GPI in 0.1 ml PBS, prepared from purified human Beta2GPI as described above.

Proliferation was assayed ten days after immunization with the Beta2GPI as follows: Draining inguinal lymph nodes were prepared by meshing the tissues on 100 mesh screens. Red blood cells were lysed with cold sterile double distilled water (6 ml) for 30 seconds and 2 ml of NaCl 3.5% was added. Incomplete medium was added (10 ml), cells were centrifuged for 7 min at 1,700 rpm, resuspended in RPMI medium and counted in a haemocytometer at 1:20 dilution (10 μl cells+190 μl Trypan Blue). Proliferation was measured by the incorporation of [$^3$H] Thymidine into DNA in triplicate samples of 100 μl of the packed cells (1×10$^6$ cells/ml) in a 96 well microtiter plate. Triplicate samples of Beta2GPI (10 μg/ml, 100 μl/well) were added, cells incubated for 72 hours (37° C., 5%, $CO_2$ and ~98% humidity) and 10 μl $^3$[H] Thymidine (0.5 μCi/well) was added. After an additional day of incubation the cells were harvested and transferred to glass fiber filters using a cell harvester (Brandel) and counted using β-counter (Lumitron). Proliferation was measured by the incorporation of [$^3$H] thymidine into DNA during the final 12 h of incubation. The results are expressed as the stimulation index (S.I.): the ratio of the mean radioactivity (cpm) of the antigen to the mean background (cpm) obtained in the absence of the antigen. Standard deviation was always <10% of the mean cpm.

Statistical Analysis: A one-way ANOVA test was used to compare independent values. $p<0.05$ was accepted as statistically significant.

Example 1

Inhibition of Atherogenesis in Genetically Predisposed (Apo-E-Deficient) Mice by Induction of Nasal Tolerance with Low Doses of the Plaque Associated Molecules Oxidized LDL, Human Beta2GPI and HSP 65

The present inventors here demonstrate, for the first time, that nasal exposure to low doses of the plaque associated molecules oxidized LDL, Beta2GPI and HSP 65 provides induction of tolerance to the antigens, and significant inhibition of atherogenesis. Thus, nasal exposure to purified, oxidized human LDL, human Beta2GPI and recombinant mycobacterial HSP 65 were compared for their effectiveness in suppressing atherogenesis in Apo-E-deficient mice. 63 male 9-13 week old Apo E/C 57 mice were divided into 5 groups. In group A (HSP-65)(n=12) nasal tolerance was induced as described in Materials and Methods by administration of recombinant mycobacterial HSP 65 suspended in PBS (10 µg/mouse/10µl) for 5 days every other day. In group B (H-oxLDL)(n=14) nasal tolerance was induced as described in Materials and Methods by administration of 10 µg/mouse/10 µl oxidized purified human LDL, suspended in PBS, every other day for 5 days. Mice in group C (B2GPI) (n=13) received 10 µg/mouse/10 µl human Beta2GPI per mouse, administered intranasally as described in Materials and Methods, every other day for 5 days. Mice in group D (BSA)(n=12) received 10 µg/mouse/10 µl bovine serum albumin (BSA) per mouse, administered intranasally as described in Materials and Methods, every other day for 5 days. Mice in group E (PBS)(n=12) received 10 µl PBS per mouse, administered intranasally. Mice were bled prior to feeding (Time 0) and at the conclusion of the experiment (End) for determination of lipid profile. Atherosclerosis was assessed in heart and aorta as described above, 8 weeks after the last feeding. Mice were weighed every 2 weeks during the experiment. All mice were fed water ad libitum and a normal chow-diet containing 4.5% fat by weight (0.02% cholesterol), up to the final antigen exposure, and then a "Western" diet until sacrifice.

tolerance has no significant effect on other general parameters measured, such as weight gain, triglyceride or cholesterol blood levels. Thus, the antigenic plaque associated molecules oxidized LDL, Beta2GPI and HSP 65 are highly potent inducers of nasal tolerance, with surprisingly low doses (10 µg/mouse) and brief exposure (3 days) of significant (greater than 65%) and consistent protection from atherogenesis in these genetically susceptible Apo-E-deficient mice.

Example 2

Superior Inhibition of Atherogenesis in Genetically Predisposed (Apo-E-Deficient) Mice by Induction of Nasal Tolerance with HSP 65

The present inventors here demonstrate, for the first time, that nasal exposure to exceedingly low doses of the plaque associated molecule HSP 65 provides superior induction of tolerance to the antigen, and inhibition of atherogenesis. Thus, nasal exposure to a low dose and an exceedingly low dose of recombinant human HSP 65 were compared for their effectiveness in suppressing atherogenesis in Apo-E-deficient mice. 58 male 12-16 week old Apo E/C 57 mice were divided into 4 groups. In group A (HSP-65 high)(n=14) nasal tolerance was induced as described in Materials and Methods by intranasal administration of 10 g/mouse/10 µl recombinant human HSP 65 suspended in PBS for 5 days every other day. In group B (HSP-65 low)(n=16) nasal tolerance was induced as described in Materials and Methods by administration of 1 µg/mouse/10 µl recombinant human HSP

TABLE 1

Inhibition of atherogenesis in Apo-E-deficient mice by intranasal administration of exceedingly low doses of plaque associated molecules

| | | HSP-65 | H-oxLDL | H-B2-GPI | BSA | PBS | |
|---|---|---|---|---|---|---|---|
| Time 0 | Weight (gr) (Mean ± S.E) | 22.6 ± 0.8 | 22.3 ± 0.5 | 22.3 ± 0.7 | 21.8 ± 0.7 | 21.7 ± 0.5 | P = 0.833 |
| | Chol (mg/dL) (Mean ± S.E) | 237 ± 13 | 230 ± 10 | 230 ± 14 | 236 ± 19 | 227 ± 14 | P = 0.986 |
| | TG (mg/dL) (Mean ± S.E) | 150 ± 19 | 178 ± 17 | 162 ± 18 | 185 ± 22 | 160 ± 15 | P = 0.664 |
| END | Weight (gr) (Mean ± S.E) | 26.8 ± 0.9 | 28.2 ± 1.0 | 29.2 ± 1.5 | 25.5 ± 1.0 | 26.3 ± 1.3 | P = 0.157 |
| | Chol (mg/dL) (Mean ± S.E) | 1181 ± 114 | 1611 ± 119 | 1601 ± 125 | 1470 ± 183 | 1606 ± 181 | P = 0.197 |
| | TG (mg/dL) (Median) | 288 | 275 | 380 | 315 | 403 | P = 0.416 |
| | Sinus Lesion (µm$^2$) (Mean ± S.E) | 44375 ± 5437 | 43393 ± 4107 | 46250 ± 4486 | 120500 ± 8746 | 128182 ± 9102 | P < 0.001 |

Note:
"Weight" is weight in grams; "Chol" is serum cholesterol and "TG" is serum triglycerides, expressed in mg/dL.

Figure 1:
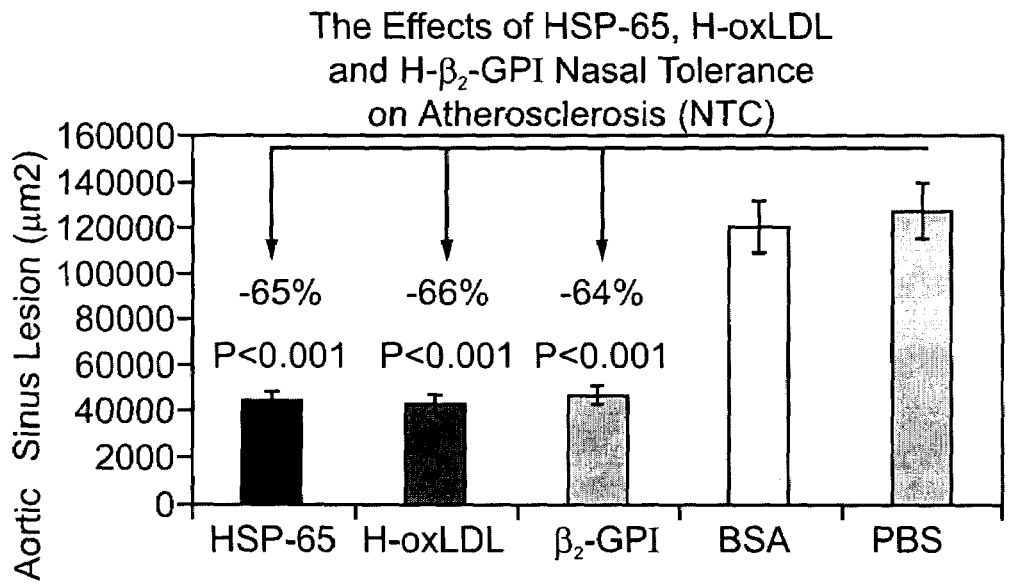
FIG. 1 illustrates inhibition of early atherogenesis in apo-E deficient mice by nasal tolerance induced by administration of low doses of plaque associated molecules. 9-13 week old apo-E deficient mice were exposed intranasally, with mild sedation, to 3 doses of 10 μg/mouse each HSP 65 (HSP-65)(n=12), human oxidized LDL (H-oxLDL)(n=14), human Beta2GPI (B2 gpi)(n=13), bovine serum albumin (BSA) or sham exposure to saline (PBS)(n=12). All mice received the atherogenic "Western" diet following last exposure. Atherogenesis is expressed as the area of atheromatous lesions in the aortic sinus 5 weeks following the $3^{rd}$ exposure.

As can be seen from FIG. 1, the results depicted in Table 1 demonstrate the strikingly effective inhibition of atherogenesis measured in the tissues of mice receiving nasal exposure to low doses (10 µg/mouse) of the plaque associated molecules, compared to control mice exposed to sham antigen (BSA) or PBS. Furthermore, nasal tolerance is specific in its mode of protection: clearly, induction of nasal 65 suspended in PBS every other day for 5 days. Mice in group C (BSA)(n=14) received 1 µg/mouse/10 µl BSA per mouse, administered intranasally, every other day for 5 days. Mice in group D (PBS)(n=14) received 10 µl PBS per mouse, administered intranasally. Mice were bled prior to feeding (Time 0) and at the conclusion of the experiment (End) for determination of lipid profile. Atherosclerosis was assessed in heart and aorta as described above, 8 weeks after the last feeding. Mice were weighed every 2 weeks during the experiment. All mice were fed water ad libitum and a normal chow-diet containing 4.5% fat by weight (0.02% cholesterol), up to the final antigen exposure, and then a "Western" diet until sacrifice.

TABLE 2

Superior inhibition of atherogenesis in Apo-E-deficient mice by intranasal administration of human HSP 65

|  |  | HSP6S 10 μg/Mouse N = 12 | HSP65 1 μg/Mouse N = 16 | BSA 100 μg/Mouse N = 11 | PBS N = 10 | Statistics |
|---|---|---|---|---|---|---|
| End | Wt | 28.4 ± 1.0 | 26.9 ± 0.9 | 27.7 ± 0.5 | 28.7 ± 0.7 | P = 0.363 |
|  | Chol | 1073 ± 65 | 1010 ± 64 | 1009 ± 74 | 1015 ± 85 | P = 0.897 |
|  | TG | 348 ± 32 | 315 ± 46 | 316 ± 32 | 390 ± 44 | P = 0.564 |
|  | Sinus Les. μm$^2$ | 22292 ± 2691 | 17109 ± 2053 | 54432 ± 8201 | 47750 ± 5779 | P < 0.05 Between HSP-65 and PBS or BSA |

Note:
"Weight" is weight in grams; "Chol" is serum cholesterol and "TG" is serum triglycerides, expressed in mg/dL.

Figure 2:
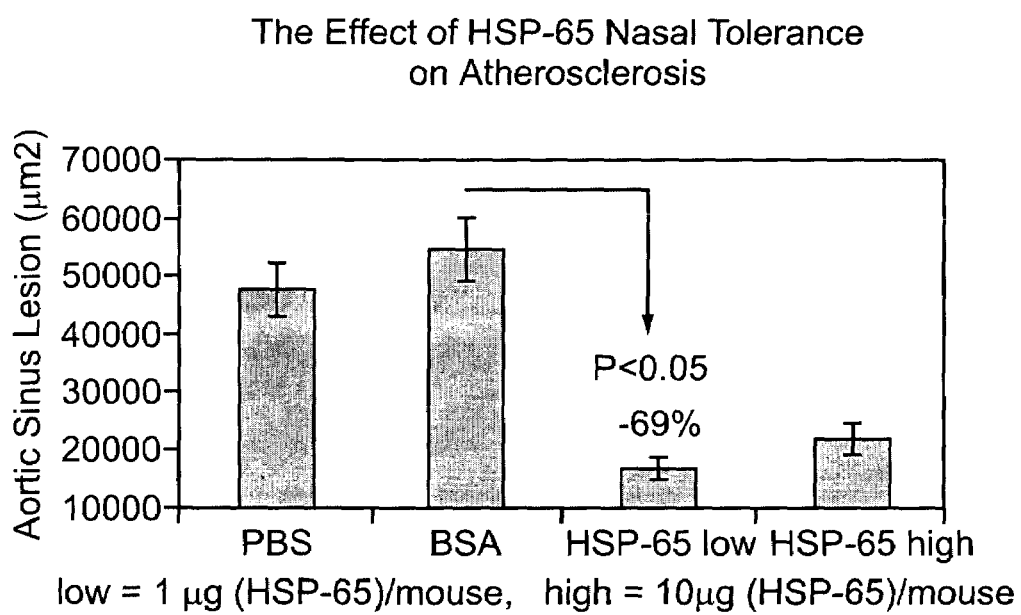
FIG. 2 illustrates superior inhibition of early atherogenesis in apo-E deficient mice by mucosal tolerance induced by intranasal exposure to exceedingly low doses of HSP 65. Nasal tolerance was induced in 12-16 week old apo-E deficient mice by intranasal administration of 3 doses of 1 μg/mouse HSP65 (HSP-65 low)(n=16) or 10 μg/mouse HSP65 (HSP-65 high)(n=14) every other day for 5 days.

As can be seen from FIG. 2, the results depicted in Table 2 demonstrate the superior effectiveness of inhibition of atherogenesis measured in the tissues of mice receiving nasal exposure to exceedingly low doses (1 μg/mouse) of HSP 65, compared to control mice exposed to sham antigen (BSA) or PBS. Furthermore, nasal tolerance is specific in its mode of protection: clearly, induction of nasal tolerance has no significant effect on other general parameters measured, such as weight gain, triglyceride or cholesterol blood levels. Thus, the antigenic plaque associated molecule HSP 65 is an extremely potent inducer of nasal tolerance, with even exceedingly low doses conferring significant (approximately 70%) protection from atherogenesis in genetically susceptible Apo-E-deficient mice, greatly superior to the protection achieved by induction of oral tolerance (30%; see U.S. patent application Ser. No. 09/806,400 to Shoenfeld et al filed Sep. 30, 1999).

Example 3

Superior Suppression of Specific Anti-Beta2GPI Immune Reactivity in Genetically Predisposed (apo-E Deficient) Mice by Intranasal Administration of Human Beta2GPI Tolerance induced by mucosal exposure to plaque associated molecules may be mediated by suppression of specific immune responses to antigenic portions of these plaque associated molecules. Lymphocyte proliferation in response to mucosal (nasal and oral) exposure to human Beta2GPI was measured in Apo-E-deficient mice. 9 male, 5 week old Apo E/C 57 deficient mice were divided into 3 groups. In group A (n=3) oral tolerance was induced with 100 μg/mouse Beta2GPI suspended in 0.2 ml PBS, administered by gavage, as described above, every other day for 5 days. In group B (n=3) nasal tolerance was induced with 10 μg/mouse Beta2GPI suspended in 10 μl PBS, administered intranasally as described above, every other day for 5 days. The mice in group C (n=3) received oral administration of 200 μl PBS every other day for 5 days. Immune reactivity was stimulated in all mice by immunization with human Beta2GPI as described above in the Materials and Methods section, one day after the last feeding. Ten days after the immunization lymph nodes were collected for assay of proliferation. All mice were fed normal chow-diet containing 4.5% fat by weight (0.02% cholesterol) and water ad libitum.

TABLE 3

Intranasal pretreatment with purified human beta2 GPI suppresses immune response to Human Beta2GPI in Apo-E-deficient mice

|  | PBS | H-β$_2$-GPI OT | H-β$_2$-GPI NT |
|---|---|---|---|
| S.I (Stimulation Index) | 7.0 ± 0.2 | 4.4 ± 0.5 | 2.1 ± 0.5 |

As can be seen from FIG. 3, the results depicted in Table 3 demonstrate significant suppression of immune reactivity to human Beta2GPI antigen, measured by inhibition of proliferation in the lymph nodes of Apo-E-deficient mice. Lymphocytes from mice receiving intranasal exposure to low atherogenesis-inhibiting doses (10 μg/mouse) of human Beta2GPI showed an exceedingly reduced stimulation index following immunization with Beta2GPI, as compared to orally exposed and control (PBS) mice. Since previous studies with induction of nasal tolerance have shown no significant effect on other parameters measured, such as weight gain, triglyceride or cholesterol blood levels, or immune competence (see above-mentioned Examples), these results indicate a specific suppression of anti-Beta2GPI immune reactivity. Thus, intranasal administration of the purified plaque associated molecule Beta2GPI is a superior method of attenuating the cellular immune response to immunogenic and atherogenic plaque associated molecules in these genetically susceptible Apo-E-deficient mice.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. A method of treatment of atherosclerosis, cardiovascular disease, cerebrovascular disease, peripheral vascular disease, stenosis, restenosis and/or in-stent-stenosis in a subject in need thereof, the method comprising mucosally administering a therapeutically effective amount of at least one plaque associated molecule to the subject, wherein said plaque associated molecule is selected from the group consisting of an oxidized low density lipoprotein, a heat shock protein 60/65 and a β-2 glycoprotein 1, and wherein said administration at least one plaque associated molecule reduces an immune reactivity to said at least one plaque associated molecule in said subject.

2. The method of claim 1, wherein said at least one plaque associated molecule is a naturally occurring or synthetic molecule.

3. The method of claim 1, wherein administration of said at least one plaque associated molecule is effected via nasal, respiratory, otic and/or conjunctival route.

4. The method of claim 1, wherein said at least one plaque associated molecule is administered along with a therapeutically effective amount of a compound selected from the group consisting of HMGCoA reductase inhibitors (statins), mucosal adjuvants, corticosteroids, anti-inflammatory compounds, analgesics, growth factors, toxins, and additional tolerizing antigens.

5. The method of claim 1, wherein said plaque associated molecule is oxidized low density lipoprotein.

6. The method of claim 1, wherein said plaque associated molecule is β-2 glycoprotein 1.

7. The method of claim 1, wherein said plaque associated molecule is heat shock protein 60/65.

8. The method of claim 7, wherein said heat shock protein 60/65 is a human heat shock protein 60/65.

* * * * *